United States Patent
Seelig

(10) Patent No.: US 9,814,498 B2
(45) Date of Patent: Nov. 14, 2017

(54) APPARATUS AND METHODS FOR REDUCTION OF VERTEBRAL BODIES IN A SPINE

(71) Applicant: Zimmer Spine, Inc., Minneapolis, MN (US)

(72) Inventor: Matthew E. Seelig, Austin, TX (US)

(73) Assignee: Zimmer Spine, Inc., Edina, MN (US)

( * ) Notice: Subject to any disclaimer, the term of this patent is extended or adjusted under 35 U.S.C. 154(b) by 77 days.

(21) Appl. No.: 14/741,839

(22) Filed: Jun. 17, 2015

(65) Prior Publication Data

US 2015/0272632 A1 Oct. 1, 2015

Related U.S. Application Data

(63) Continuation of application No. 14/223,119, filed on Mar. 24, 2014, now Pat. No. 9,084,648, which is a continuation of application No. 11/567,889, filed on Dec. 7, 2006, now Pat. No. 8,679,128.

(51) Int. Cl.
| | |
|---|---|
| *A61B 17/70* | (2006.01) |
| *A61B 17/88* | (2006.01) |
| *A61B 90/00* | (2016.01) |

(52) U.S. Cl.
CPC ...... *A61B 17/7086* (2013.01); *A61B 17/8866* (2013.01); *A61B 17/7032* (2013.01); *A61B 2090/037* (2016.02)

(58) Field of Classification Search
CPC .. A61B 17/70; A61B 17/7086; A61B 17/8866
See application file for complete search history.

(56) References Cited

U.S. PATENT DOCUMENTS

| | | | |
|---|---|---|---|
| 5,484,440 A | 1/1996 | Allard | |
| 5,681,319 A * | 10/1997 | Biedermann | ...... A61B 17/7037 606/104 |
| 5,733,286 A | 3/1998 | Errico et al. | |
| (Continued) | | | |

FOREIGN PATENT DOCUMENTS

WO    WO-2006036324 A2    4/2006

OTHER PUBLICATIONS

"U.S. Appl. No. 11/567,889, Advisory Action dated Mar. 27, 2012", 2 pgs.

(Continued)

*Primary Examiner* — Christopher Beccia
(74) *Attorney, Agent, or Firm* — Schwegman Lundberg & Woessner, P.A.

(57) ABSTRACT

A system for reduction of vertebral bodies (or vertebrae) in various embodiments includes a reducer, and extender, and a hollow tube. The reducer couples to the extender, which in turn couples to an elongated member, such as a rod, and to a bone fastener assembly. The reducer allows reduction of the vertebral body incrementally, and by a desired amount. The reducer may include or may be used in conjunction with a holding device or holder in order to hold or keep the amount of reduction constant or steady once the desired amount of reduction has been obtained. The reducer may use one of several embodiments, including embodiments that use threaded assemblies or members, inclining members or wedges, offset cams, scissor jacks, and/or levers.

20 Claims, 21 Drawing Sheets

(56) References Cited

U.S. PATENT DOCUMENTS

| | | | |
|---|---|---|---|
| 5,910,141 A * | 6/1999 | Morrison | A61B 17/7088 606/101 |
| 6,139,549 A | 10/2000 | Keller | |
| 6,183,472 B1 | 2/2001 | Lutz | |
| 6,440,133 B1 * | 8/2002 | Beale | A61B 17/7086 606/104 |
| 6,458,132 B2 | 10/2002 | Choi | |
| 6,488,681 B2 | 12/2002 | Martin et al. | |
| 6,530,929 B1 * | 3/2003 | Justis | A61B 17/00234 606/103 |
| 6,554,834 B1 | 4/2003 | Crozet et al. | |
| 6,648,888 B1 * | 11/2003 | Shluzas | A61B 17/7091 606/86 A |
| 6,716,214 B1 | 4/2004 | Jackson | |
| 6,743,231 B1 * | 6/2004 | Gray | A61B 17/7001 606/279 |
| 6,755,829 B1 | 6/2004 | Bono et al. | |
| 6,974,460 B2 | 12/2005 | Carbone et al. | |
| 7,179,261 B2 * | 2/2007 | Sicvol | A61B 17/7032 606/86 A |
| 7,520,879 B2 | 4/2009 | Justis et al. | |
| 7,597,694 B2 | 10/2009 | Lim et al. | |
| 7,771,430 B2 * | 8/2010 | Jones | A61B 17/7086 606/279 |
| 8,679,128 B2 * | 3/2014 | Seelig | A61B 17/7086 606/90 |
| 9,084,648 B2 | 7/2015 | Seelig | |
| 2003/0199872 A1 | 10/2003 | Markworth et al. | |
| 2003/0236529 A1 | 12/2003 | Shluzas et al. | |
| 2004/0147937 A1 * | 7/2004 | Dunbar, Jr. | A61B 17/7091 606/99 |
| 2006/0089651 A1 * | 4/2006 | Trudeau | A61B 17/7086 606/86 R |
| 2006/0095035 A1 * | 5/2006 | Jones | A61B 17/7037 606/57 |
| 2006/0111713 A1 * | 5/2006 | Jackson | A61B 17/7037 606/914 |
| 2006/0247630 A1 * | 11/2006 | Iott | A61B 17/701 606/86 A |
| 2008/0009864 A1 | 1/2008 | Forton et al. | |

OTHER PUBLICATIONS

"U.S. Appl. No. 11/567,889, Advisory Action dated Dec. 21, 2010", 3 pgs.

"U.S. Appl. No. 11/567,889, Examiner Interview Summary dated May 9, 2012", 3 pgs.

"U.S. Appl. No. 11/567,889, Final Office Action dated Jan. 4, 2012", 12 pgs.

"U.S. Appl. No. 11/567,889, Final Office Action dated Oct. 7, 2010", 10 pgs.

"U.S. Appl. No. 11/567,889, Final Office Action dated Oct. 7, 2013", 9 pgs.

"U.S. Appl. No. 11/567,889, Non Final Office Action dated Mar. 5, 2010", 8 pgs.

"U.S. Appl. No. 11/567,889, Non Final Office Action dated May 30, 2013", 8 pgs.

"U.S. Appl. No. 11/567,889, Non Final Office Action dated Aug. 3, 2011", 9 pgs.

"U.S. Appl. No. 11/567,889, Notice of Allowance dated Nov. 6, 2013", 8 pgs.

"U.S. Appl. No. 11/567,889, Pre-Brief Appeal Conference decision dated May 25, 2011", 2 pgs.

"U.S. Appl. No. 11/567,889, Pre-Brief Conference request filed Jan. 7, 2011", 6 pgs.

"U.S. Appl. No. 11/567,889, Response filed Jan. 5, 2010 to Restriction Requirement dated Dec. 9, 2009", 6 pgs.

"U.S. Appl. No. 11/567,889, Response filed Mar. 2, 2012 to Final Office Action dated Jan. 4, 2012", 9 pgs.

"U.S. Appl. No. 11/567,889, Response filed May 4, 2012 to Advisory Action dated Mar. 27, 2012", 14 pgs.

"U.S. Appl. No. 11/567,889, Response filed Jul. 6, 2010 to Non Final Office Action dated Mar. 5, 2010", 9 pgs.

"U.S. Appl. No. 11/567,889, Response filed Aug. 29, 2013 to Non Final Office Action dated May 30, 2013", 8 pgs.

"U.S. Appl. No. 11/567,889, Response filed Oct. 28, 2013 to Final Office Action dated Oct. 7, 2013", 8 pgs.

"U.S. Appl. No. 11/567,889, Response filed Nov. 3, 2011 to Non Final Office Action dated Aug. 3, 2011", 8 pgs.

"U.S. Appl. No. 11/567,889, Response filed Dec. 6, 2010 to Final Office Action dated Oct. 7, 2010", 11 pgs.

"U.S. Appl. No. 11/567,889, Restriction Requirement dated Dec. 9, 2009", 7 pgs.

"International Application Serial No. PCT/US2007/085160, International Search Report dated Apr. 9, 2008", 3 pgs.

* cited by examiner

APPARATUS AND METHODS FOR REDUCTION OF VERTEBRAL BODIES IN A SPINE

CROSS-REFERENCE TO RELATED APPLICATIONS

The present application is a continuation of U.S. patent application Ser. No. 14/223,119, filed Mar. 24, 2014, which is a continuation of U.S. patent application Ser. No. 11/567,889, filed Dec. 7, 2006, now U.S. Pat. No. 8,679,128, issue date Mar. 25, 2015, the complete disclosure of which is herein incorporated by reference.

TECHNICAL FIELD

The present invention generally relates to apparatus and methods used during a spinal surgical procedure. More particularly, the inventive concepts relate to spinal surgical procedure that use apparatus and methods for reducing vertebral bodies.

BACKGROUND

Modern spine surgery often involves the use of spinal implants to correct or treat various spine disorders or to support the spine. Spinal implants may help, for example, to stabilize the spine, correct deformities of the spine, facilitate fusion, treat spinal fractures, repair annular defects, etc.

Spinal implant systems for a lumbar region of the spine may be inserted during a procedure using a posterior spinal approach. Conventional systems and methods for such operations may involve dissecting and retracting soft tissue near or around the surgical site, which may cause trauma to the soft tissue, and extend recovery time.

Minimally invasive procedures and systems may reduce recovery time as well as trauma to the soft tissue surrounding a stabilization site. During minimally invasive surgical procedures, often a reduction of one of more vertebrae are indicated. A need exists for reduction apparatus and related methods that provide flexibility of operation, enhanced range of reduction, and adaptability to the patient's anatomy.

SUMMARY

The disclosed inventive concepts relate to apparatus and methods for reduction of vertebrae or vertebral bodies. In one exemplary embodiment, an apparatus according to the invention includes a reducer, and an extender coupled releasably to the reducer. The reducer includes a sleeve and a knob. The sleeve has a threaded portion. Similarly, the knob has a threaded portion that is in engagement with the threaded portion of the sleeve to provide reduction of the vertebra or vertebral body.

In another exemplary embodiment, a system for reducing a vertebra or vertebral body includes an extender and a reducer. The reducer is releasably coupled to the extender, and is configured to allow incremental reduction of the vertebral body.

Yet another exemplary embodiment relates to a method of reducing a vertebra or vertebral body. The method includes moving incrementally one member with respect to a second member. The first member is releasably coupled to the vertebra, which results in the reduction of the vertebra or vertebral body.

BRIEF DESCRIPTION OF THE DRAWINGS

The appended drawings illustrate only exemplary embodiments of the invention and therefore should not be considered or construed as limiting its scope. Persons of ordinary skill in the art who have the benefit of the description of the invention appreciate that the disclosed inventive concepts lend themselves to other equally effective embodiments. Unless noted otherwise, in the drawings, the same numeral designators used in more than one drawing denote the same, similar, or equivalent functionality, components, or blocks.

DETAILED DESCRIPTION

The disclosed novel concepts relate to apparatus and methods for reducing vertebrae or vertebral bodies during minimally invasive surgical procedures, for example, during a spinal stabilization procedure. Details of minimally invasive surgery are described in detail in U.S. patent application Ser. No. 10/980,675, titled "Instruments and Methods for Reduction of Vertebral Bodies," filed on Nov. 3, 2004, and incorporated by reference in this application. Briefly, minimally invasive surgery uses apparatus such as guide wires, bone fastener assemblies, extenders, and sleeves, as described in detail in U.S. patent application Ser. No. 10/980,675, referenced above.

Figure 1A:
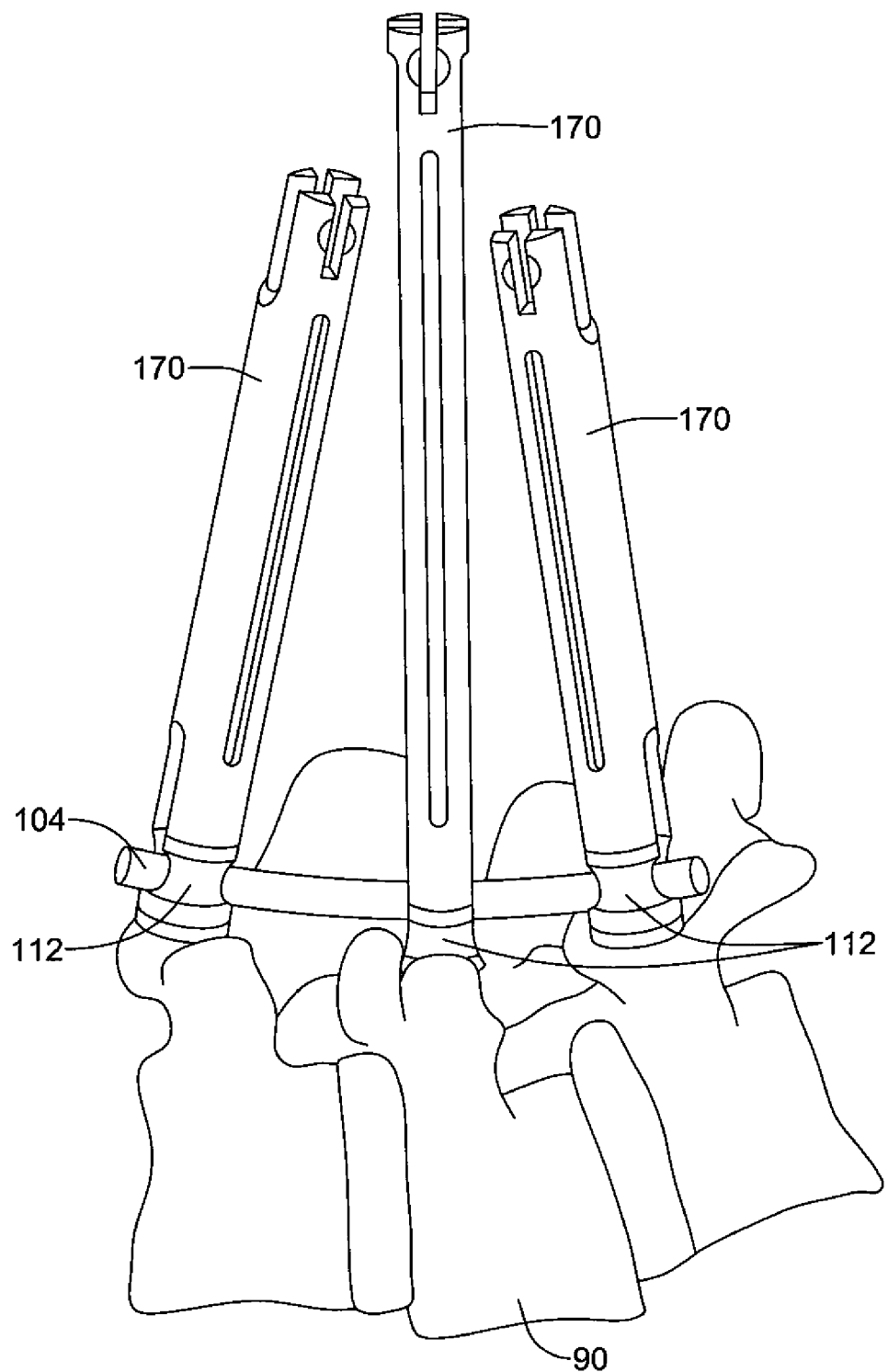
FIGS. 1A and 1B show details of how a typical reduction procedure brings into alignment a misaligned vertebra.
Figure 1B:
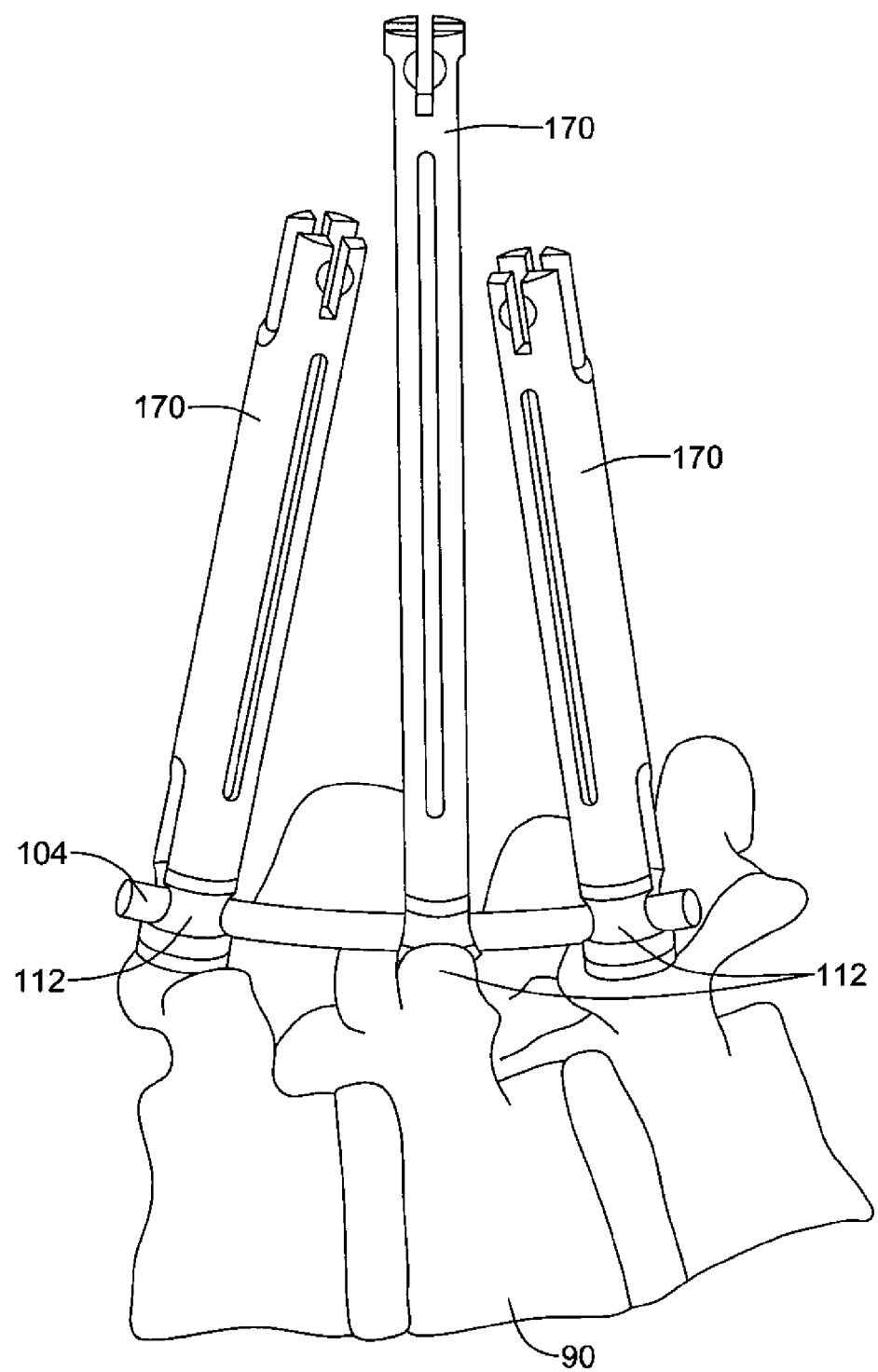

During minimally invasive surgery, a reduction of one or more vertebral bodies is indicated. As persons of ordinary skill in the art who have the benefit of the description of the invention understand, reduction generally refers to the replacement or realignment of a body part in normal position or restoration of a bodily condition to normal. FIGS. 1A and 1B show details of how a typical reduction procedure brings into alignment a misaligned vertebra.

More specifically, in FIG. 1A, vertebral body 90 is out of alignment with the rest of the spine and is to be returned to its original position via a reduction procedure. To do so, the surgeon constructs a "framework" or assembly that will serve as the alignment point. The surgeon constructs the framework with pedicle screws or other suitable fasteners and a rod or elongated member to bridge the "bad" (defective or diseased) segment or vertebra and anchoring to the two "good" (healthy and properly aligned) adjacent segments or vertebrae above and below.

The surgeon places fasteners or pedicle screws (collar 112 of the fastener assembly is shown explicitly) into the desired vertebral bodies, including the "bad" segment (labeled 90). Once in place, the surgeon locates an elongated member or rod 104 in the adjacent bone fastener assemblies (e.g., screw heads), and fastens it with a closure mechanism (e.g., closure cap). The rod is contoured in a manner that will hold the proper alignment of the segments or vertebrae once the reduction procedure is complete.

To aid in the reduction, the surgeon uses one or more extenders. Because elongated member or rod 104 passes through the middle extender (labeled 170) in the figure, which is in turn attached to the pedicle screw or fastener of the "bad" segment, the extender serves two purposes. First, the extender acts as a guide for the proper alignment of elongated member or rod 104 into the fastener assembly (e.g., screw head).

The extender also serves as a mechanism to "pull up" on the fastener or screw and consequently the vertebral body until elongated member or rod 104 is properly seated within the fastener assembly (e.g., screw head). As described below in more detail, this is done by "pushing" incrementally against elongated member or rod 104 with a hollow shaft or tube (see for example item 188 in FIGS. 2A and 2B) while "pulling" up on extender 170 in a manner similar to a tackle being used to hoist up a load.

This incremental, controlled relative motion is achieved by reducer (described below in detail). As detailed below, one part of the reducer is releasably coupled to extender 170 via locking member(s), while another part of the reducer (reduction shaft 308) is coupled to shaft or tube 188, which is in turn anchored or coupled to elongated member or rod 104.

FIG. 1B shows vertebral body 90 in its reduced state. Note that it is completely or substantially aligned with the rest of the spine or adjacent vertebral bodies. At this stage, a closure mechanism is applied that will secure, fasten, or lock elongated member or rod 104 to the bone fastener assembly (e.g., to the screw head), and therefore fix the position of the "bad" or reduced segment or vertebra 90 with respect to the adjacent segments. Bone graft may be applied to aid fusing the segments together while held in place with elongated member or rod 104 and the bone fastener assemblies.

Conventional reducers have a number of disadvantages, such as relatively limited range of operation, relative lack of adaptability to the patient's anatomy (e.g., the patient's lordotic curve), failing to allow for incremental reduction, and involving manual interaction by the surgeon at all times or substantially all times, etc.

As described here in detail, the disclosed reduction apparatus and associated methods overcome those limitations. For example, the disclosed reduction apparatus and related techniques allow incremental reduction without continual surgeon intervention, thus allowing for gradual tissue relaxation, provide relatively extended range of operation or reduction, provide quick-coupling capabilities, and adapt more easily to the patient's anatomy.

Figure 2A:
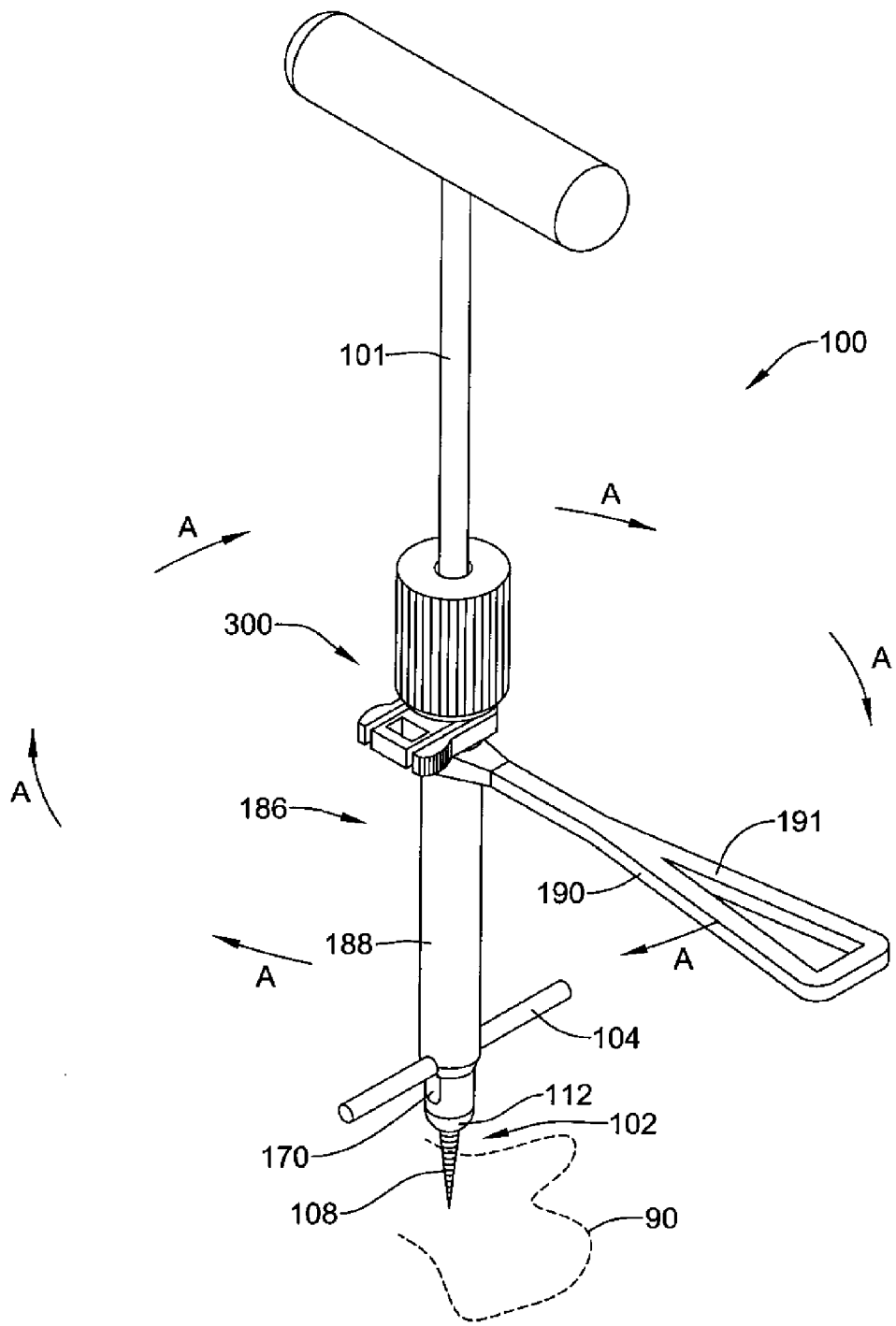
FIG. 2A shows a system for a spinal surgical operation that uses a reducer according to an exemplary embodiment of the invention.

FIG. 2A shows a shows a system 100 for a spinal surgical operation that uses a reducer according to an exemplary embodiment of the invention. System 100 includes bone fastener assembly 102 (e.g., screw, collar, and closure member (e.g., cap)), elongated member 104 (e.g., a rod), extender 170, sleeve or assembly 186, and reducer 300. Some details of system 100 are provided in U.S. patent application Ser. No. 10/980,675, referenced above.

During minimally invasive surgery, extender 170 allows the surgeon to manipulate bone fastener assembly 102 and to couple fastener 108 to vertebra 90. A distal end of an extender 170 couples to bone fastener assembly 102 and allows the surgeon to manipulate assembly 102. In the embodiment shown, extender 170 couples to collar 112 of assembly 102.

After a bone fastener assembly is coupled to extender 170, a driver may be coupled to a bone fastener of the bone fastener assembly. The driver may be used to insert the bone fastener into vertebral bone, such as vertebra 90.

Elongated member 104 allows the surgeon to accomplish a desired goal, for example, stabilize the spine, maintain the natural spacing between vertebrae, etc., as persons of ordinary skill in the art who have the benefit of the description of the invention understand. After bone fastener assemblies are installed and an elongated member is placed in the bone fastener assemblies, closure members may be secured to the bone fastener assemblies.

When a closure member is threaded on a bone fastener assembly, a counter torque wrench may be used to inhibit the application of torque to the spine of the patient. A counter torque wrench may hold an extender that is coupled to a collar. The counter torque wrench allows the application of an appropriate or desired amount of torque, for example, to shear off the tool portion of a closure member.

In some embodiments, a counter torque wrench may inhibit application of torque to a patient during tightening of a closure member and/or during shearing of a tool portion of the closure member by applying a force to an elongated member to counter the force applied to a bone fastener assembly by rotation of the closure member.

The counter torque wrench may take a variety of forms. For example, it may constitute a sleeve that includes hollow shaft or tube 188. Hollow shaft 188 may be inserted through an opening in the body over extender 170 and advanced toward the patient's spine.

Handle 190 of sleeve or assembly 186 may have of various shapes or designs, as desired. In some embodiments, a shape of handle 190 may facilitate gripping of sleeve or assembly 186 or hollow tube 188. Handle 190 may include a cut-out portion to facilitate gripping and/or to reduce the weight of the sleeve. In certain embodiments, a shape of handle 190 may be tapered toward hollow shaft 188 to reduce interference and/or increase visibility of a surgical site.

In the embodiment shown, handle 190 includes lock button or mechanism 191. During normal operation, lock mechanism 191 locks or holds the position of handle 190 with respect to sleeve or assembly 186 or hollow shaft 188. By pulling back lock button 191, the surgeon may "flip" handle 190 around (i.e., move it along the path shown by arrows labeled A) in order to reduce interference with the patient's body and/or increase visibility of the surgical site.

In some embodiments, reducing one or more vertebral bodies to the shape of an elongated member (e.g., a contoured elongated member) or to a desired position may be indicated. Reduction of a vertebral body during a spinal stabilization procedure may include forcing or moving the vertebral body into a position determined by the contour of the elongated member used in the spinal stabilization system or by other indicia.

During a spinal stabilization or implant procedure, a first portion of an elongated member may be seated in a collar of a first bone fastener assembly that is coupled to a first vertebra. A closure member may be coupled to the collar and the elongated member to seat the elongated member fully in the collar and to fix the position of the elongated member relative to the first bone fastener assembly.

A second portion of the elongated member may be positioned adjacent to a collar of a second bone fastener assembly that is coupled to a second vertebra. The position of the second vertebra and/or the shape of the elongated member, however, may inhibit the second portion of the elongated member from being fully seated in the collar of the second bone fastener assembly.

A reducer may be coupled to the elongated member and to the collar of the second bone fastener assembly (e.g., via extender 170). The reducer may be used to reduce the vertebral body, e.g., fully seat the second portion of the elongated member in the collar of the second bone fastener assembly.

While the reducer holds the second portion of the elongated member seated in the collar of the second bone fastener assembly, driver 101 may be used to secure a closure member (e.g., cap or other suitable item) to the collar to fix the position of the elongated member relative to the collar. Radiological imaging or fluoroscopy may be used to determine when the reducer has fully seated the second portion of the elongated member in the collar of the second bone fastener assembly.

Reducers may be used during a minimally invasive surgical procedure or during procedures where access to an elongated member and working room are restricted. During a minimally invasive procedure or a procedure with limited access and/or limited working room, a reducer may be used to pull an extender coupled to a bone fastener assembly of a spinal implant or stabilization system upward (e.g., away from the spine) to seat the elongated member in a collar of the bone fastener assembly. Movement of a reducer may be achieved by, but is not limited to being achieved by, use of threading, cam action, linkage arms, or a combination thereof, as described below.

In some embodiments, a reducer may be used with one or more other instruments to achieve reduction of a vertebral body coupled to a spinal stabilization system. FIG. 2A depicts an embodiment of reducer 300 that may be used in combination with extender 170 and sleeve or assembly 186, including hollow shaft 188.

The reducer may be used to seat elongated member 104 in collar 112 of bone fastener assembly 102 when the bone fastener assembly is coupled to a vertebra. The reducer is designed to couple to extender 170 and pull it upward while pushing elongated member 104 into collar 112.

Without loss of generality, in one embodiment, reduction of vertebral body 90 is accomplished by moving vertebral body 90 coupled to bone fastener assembly 102 relative to elongated member 104 in such a manner that the elongated member 104 is captured within collar 112 of bone fastener assembly 102, thus holding vertebral body 90 in desired position. The reduction is accomplished by inducing relative motion of elongated member 104 with respect to collar 112 coupled to vertebral body 90 via assembly 102 or vice versa.

An apparatus for inducing relative motion is reducer 300 with engaging tabs 306 and reduction sleeve 308 that moves with respect to engaging tabs 306. Engaging tabs 306 are coupled to extender 170, which in turn is coupled to vertebral body 90 via assembly 102. Reduction sleeve 308 is coupled to hollow shaft 188, which in turn is coupled to elongated member 104. By manipulating reduction sleeve 308 with respect to engaging tabs 306, shaft 188 moves relative to extender 170. As a consequence, elongated member 104 moves relative to collar 112 of assembly 102, which is coupled to vertebral body 90.

Figure 2B:
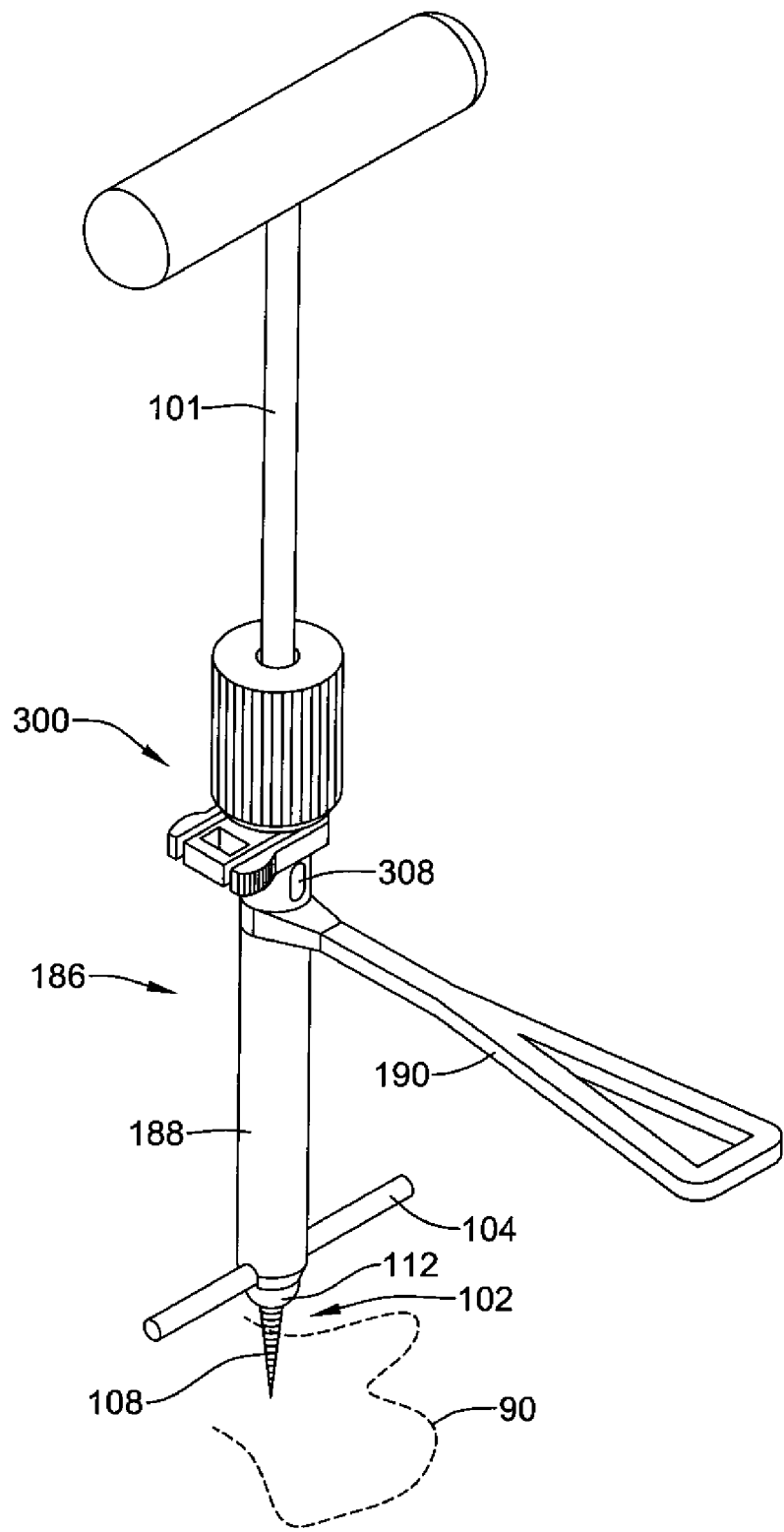
FIG. 2B illustrates reduction of a vertebral body by operating the reducer shown in FIG. 2A.

Note that the reduction apparatus uses shaft 188 and the extender 170 in order to "reach" through a small incision into the patient and manipulate elongated member 104 with respect to vertebral body 90. FIG. 2B shows elongated member 104 seated into collar 112 of assembly 102 as a result of operating reducer 300 (i.e., as a result of the reduction of vertebra or vertebral body 90, as described below in detail).

Figure 3:
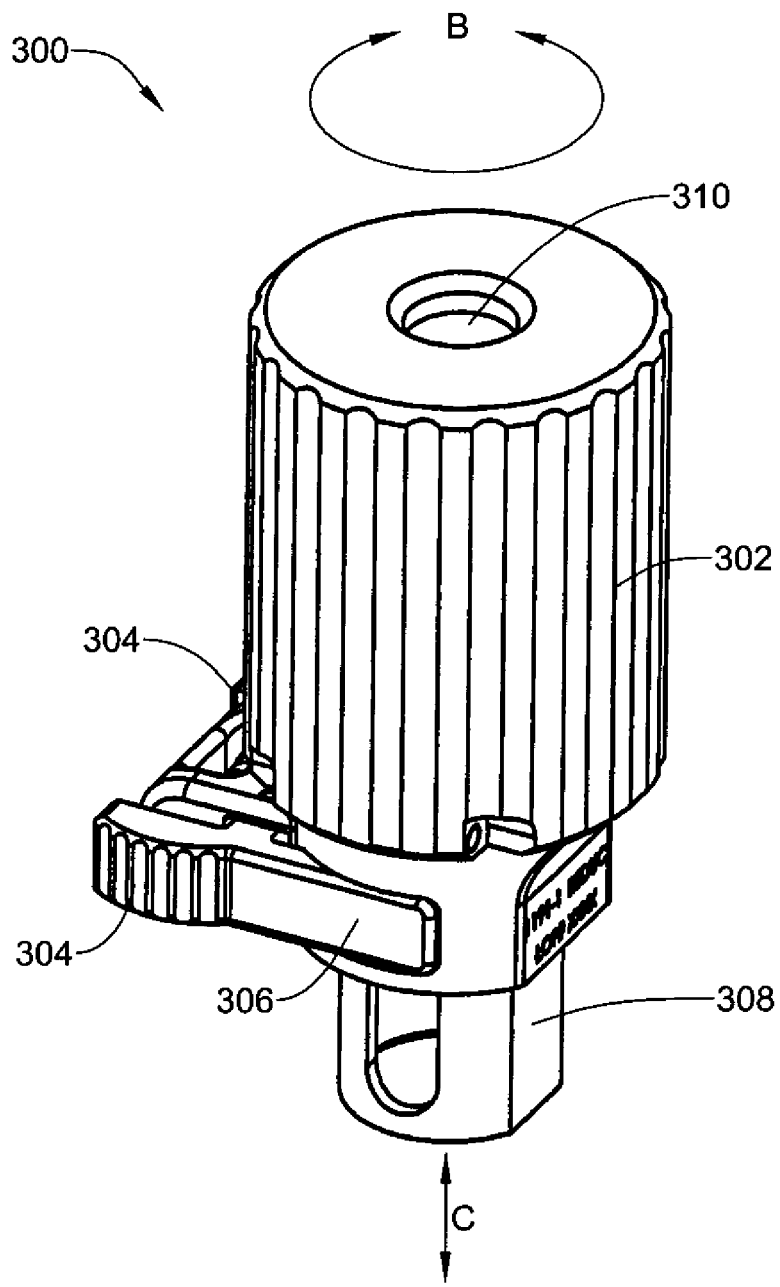
FIG. 3 depicts a reducer according to one exemplary embodiment of the invention.

FIG. 3 shows a reducer according to one exemplary embodiment of the invention. Reducer 300 includes knob or handle 302, locking handles 304, locking or engaging members or tabs 306, reduction sleeve 308, and bore 310.

Figure 4:
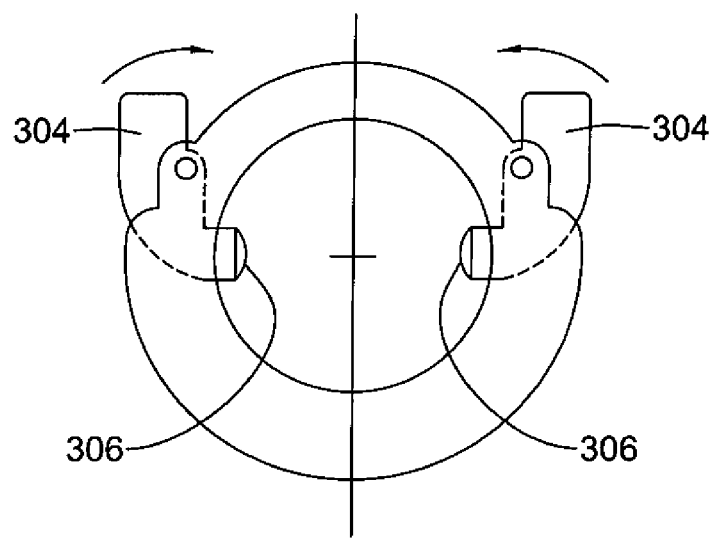
FIG. 4 shows a top view of the locking handles and locking members of the reducer in FIG. 3.

FIG. 4 shows a top view of locking handles 304 and locking members 306. Locking handles 304 include or couple to a biasing mechanism, e.g., springs to facilitate engagement of locking members 306 to extender 170. Depressing locking handles 304 causes locking members 306 to withdraw from openings in reduction sleeve 308. Releasing locking handles 304, however, causes locking members 306 to return to their original positions in the openings.

Figure 5:
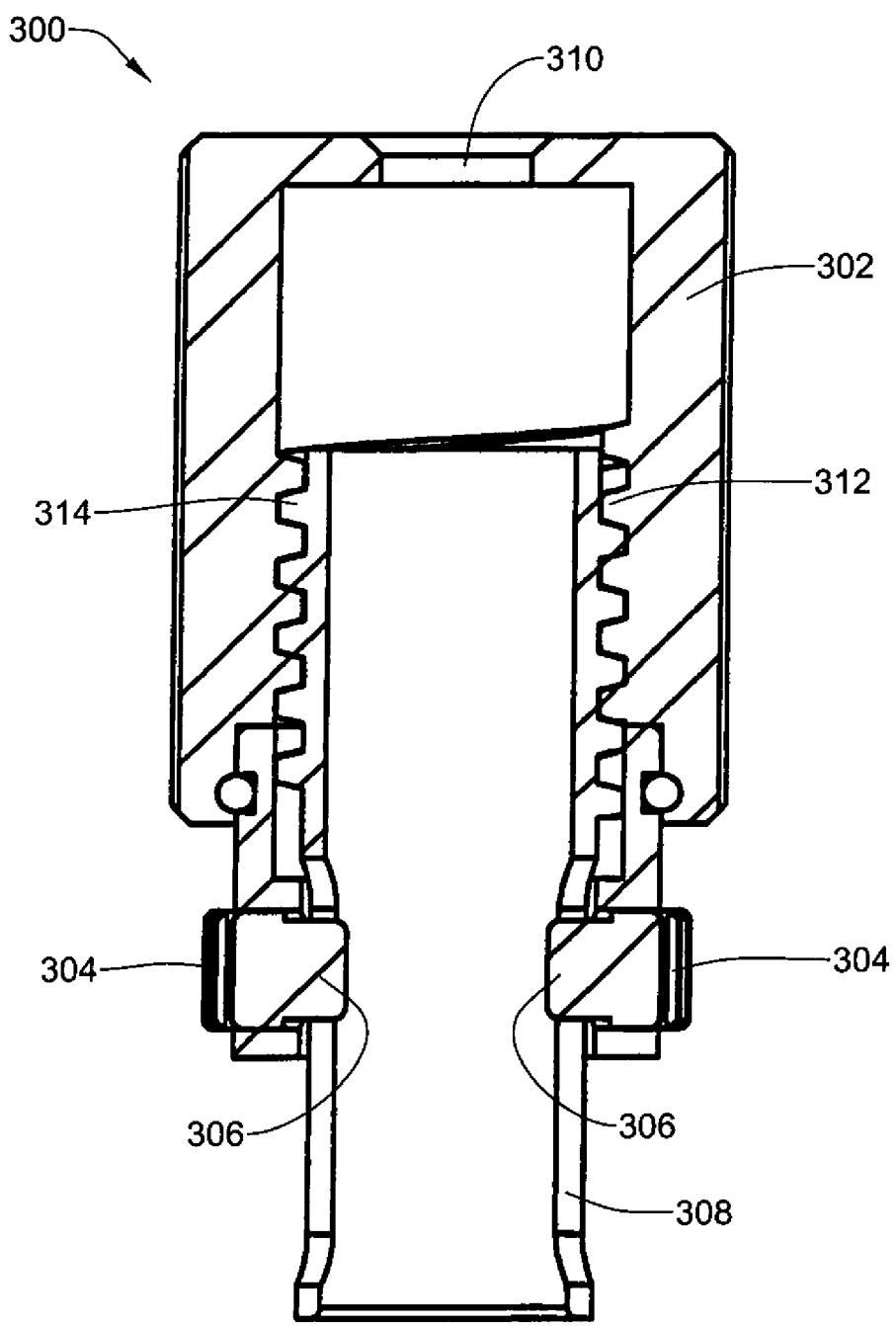
FIG. 5 illustrates a cross-section of the exemplary reducer illustrated in FIG. 3.

FIG. 5 shows a cross-section of reducer 300. Note that an inner portion or surface of knob 302 includes threads 312. An outer portion or surface of reduction sleeve 308 includes threads 314, which are complementary to threads 312 of knob 302.

Once assembled, the threads of knob 302 engage the threads of reduction sleeve 308. By rotating knob 302 along the arrows labeled "B," one may cause the coupled or engaged threads of knob 302 and reduction sleeve 308 to cause sleeve 308 to move up or down or vertically, as the arrow labeled "C" shows. The movement of sleeve 308 may in turn cause the corresponding motion of other apparatus or items coupled to it.

During minimally invasive surgery, reducer 300 couples to other surgical apparatus in order to reduce a vertebral body. For example, in one embodiment, reducer 300 couples to extender 170 (see above) via locking members 306. More specifically, by depressing locking handles 304, the surgeon causes locking members 306 to withdraw or move in an outward direction (away from sleeve 308). The surgeon then couples reducer 300 to extender 170 (e.g., by placing reduction sleeve 308 over or inside extender 170, as desired) and releases locking handles 304, as described above.

Once reducer 300 has coupled to extender 170, the surgeon may turn knob 302 in a desired direction and by a desired amount. As described above, the turning of knob 302 causes shaft 188 moves relative to extender 170. As noted, extender 170 is coupled to the bone fastener assembly 102 (see FIGS. 2A and 2B). Consequently, elongated member 104 moves relative to collar 112 of assembly 102, which is coupled to vertebral body 90, hence causing reduction of vertebral body 90.

By using relatively fine thread pitches, one may allow the surgeon to fine-tune the reduction of the vertebral bodies, as desired. For example, the surgeon may accomplish the reduction through relatively small or incremental steps. This approach provides the benefit of allowing the affected tissue to relax and helps to reduce trauma.

Furthermore, under normal circumstances, the surgeon need not continually manipulate reducer 300. Put another way, the surgeon may activate reducer 300 by a desired amount (by turning knob 302 in a desired direction and by a desired amount). Once the surgeon finishes manipulating reducer 300, it maintains the desired or final reduction.

Figure 6:
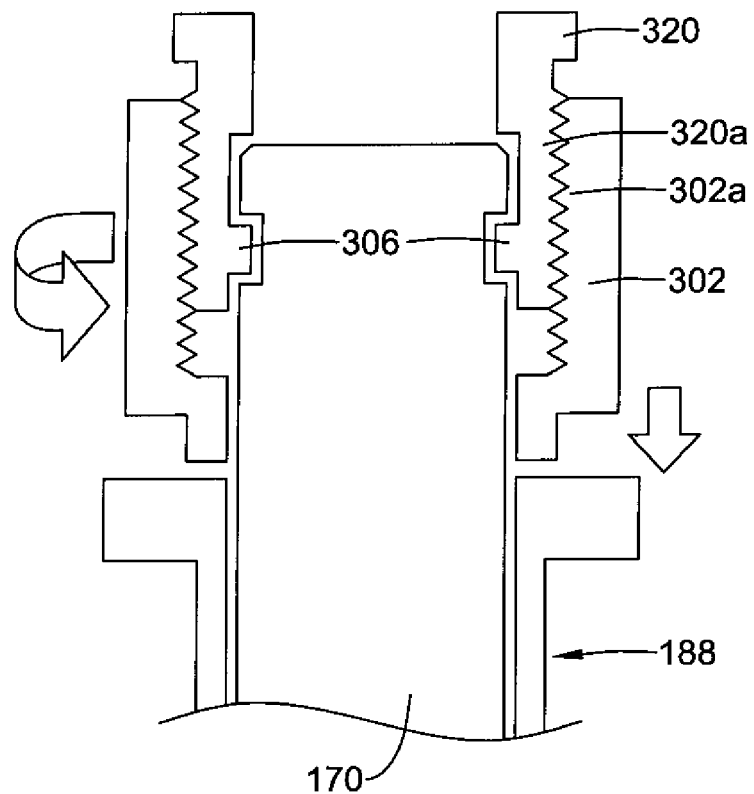
FIGS. 6-13 depict a plurality of reducers according to exemplary embodiments of the invention.

FIG. 6 shows a cross-section of another reducer according to an exemplary embodiment of the invention, coupled to extender 170 and hollow shaft 188. The reducer in FIG. 6 includes knob 302 and body 320. Body 320 couples to extender 170 through any suitable or desired mechanism, such as locking members 306.

Body 320 has a threaded portion 320A that engages a complementary threaded portion 302A of knob 302. Body 320 couples to extender 170. Turning knob 302 clockwise or counterclockwise causes body 320 and, hence, extender 170 to move up or down relative to hollow shaft 188. As a result, by turning knob 302 in a desired direction and by a desired amount, the surgeon can reduce the corresponding vertebral body.

Figure 7:
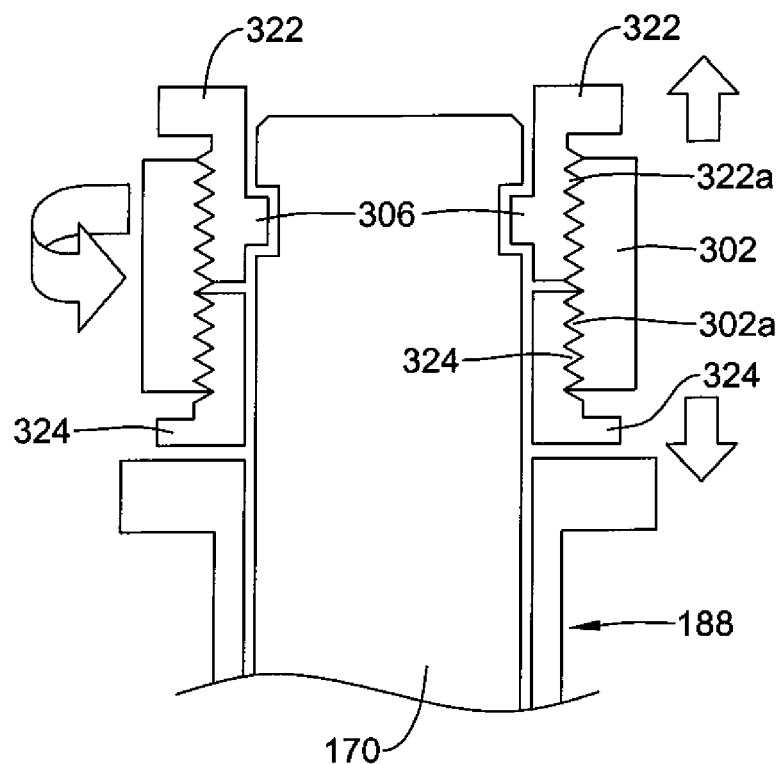

FIG. 7 shows a cross-section of another reducer according to an exemplary embodiment of the invention, coupled to extender 170 and hollow shaft 188. The reducer includes knob 302, upper body 322, and lower body 324. Upper body 322 couples to extender 170 through any suitable or desired mechanism, such as locking members 306. (Note that, alternatively, or in addition, lower body 324 may couple to extender 170, as desired, and as persons of ordinary skill in the art who have the benefit of the description of the invention understand.)

Upper body 322 has a threaded portion 322A that engages a complementary threaded portion 302A of knob 302. Similarly, lower body 324 has a threaded portion 324A that couples to threaded portion 302A of knob 302. Threaded portion 322A and threaded portion 324A have opposite thread directions. For example, in the embodiment shown, threaded portion 322A has right-hand threads, whereas threaded portion 324A has left-hand threads.

Of course, as persons of ordinary skill in the art who have the benefit of the description of the invention understand, one may use other arrangements of threads. For example, in one embodiment, threaded portion 322A may have left-hand threads and threaded portion 324A has right-hand threads.

Turning knob 302 clockwise or counterclockwise causes upper body 322 and lower body 324 to move in opposite directions. As extender 170 couples to upper body 322 (or lower body 324, as desired), movement of upper body 322 (or lower body 324) causes extender 170 to move up or down relative to hollow tube 188. As a result, by turning knob 302 in a desired direction and by a desired amount, the surgeon can reduce the corresponding vertebral body.

Figure 8:
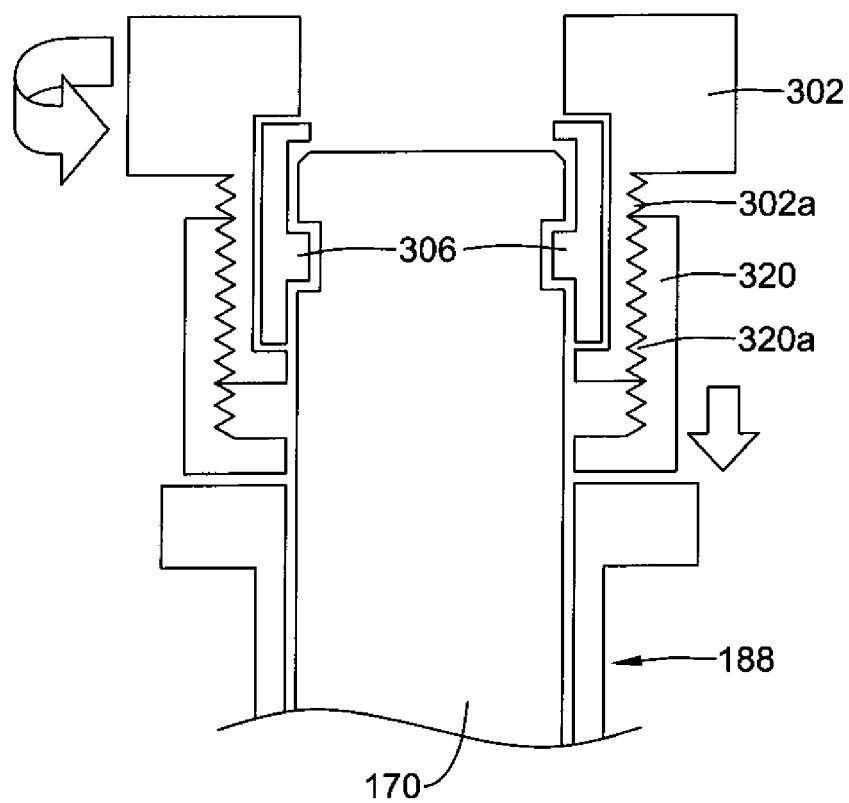

FIG. 8 shows a cross-section of another reducer according to an exemplary embodiment of the invention, coupled to extender 170 and hollow shaft 188. The reducer includes knob 302 and body 320. Body 320 couples to extender 170 through any suitable or desired mechanism, such as locking members 306.

Body 320 has a threaded portion 320A that engages a complementary threaded portion 302A of knob 302. Turning knob 302 clockwise or counterclockwise causes knob 302 to move relative to body 320. Note, however, that turning knob 302 does not change its position relative to extender 170. As extender 170 couples to knob 302, movement of knob 302 causes extender 170 to move up or down relative to hollow tube 188. Thus, by turning knob 302 in a desired direction and by a desired amount, the surgeon can reduce the corresponding vertebral body.

Figure 9:
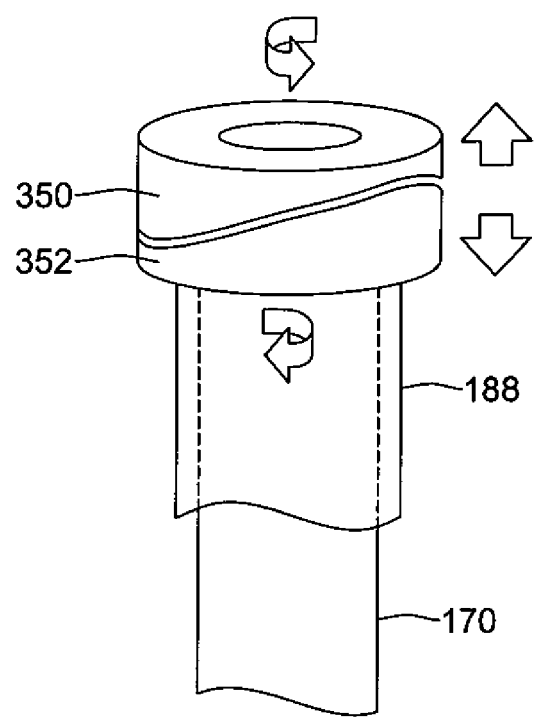

FIG. 9 illustrates a cross-section of another reducer according to an exemplary embodiment of the invention, coupled to extender 170 and hollow shaft 188. The reducer includes two progressively inclined members or wedges 350 and 352. Progressively inclined wedge 350 couples to extender 170 (via, for example, coupling members not shown explicitly). Progressively inclined wedge 352 couples to hollow shaft 188.

By turning progressively inclined wedge 350 in a desired direction and by a desired amount, while holding progressively inclined wedge 352 stationary (or vice-versa), the surgeon can cause movement of extender 172 and hence reduce the corresponding vertebral body. Note that one may use a variety of implementations of the reducer, as persons of ordinary skill in the art who have the benefit of the description of the invention understand. For example, one may use progressively inclined wedges 350 and 352 that include steps (rather than a continuously inclining profile) of desired size or height, as desired. Using stepped wedges would allow incremental reduction in discrete amounts or steps.

Figure 10:
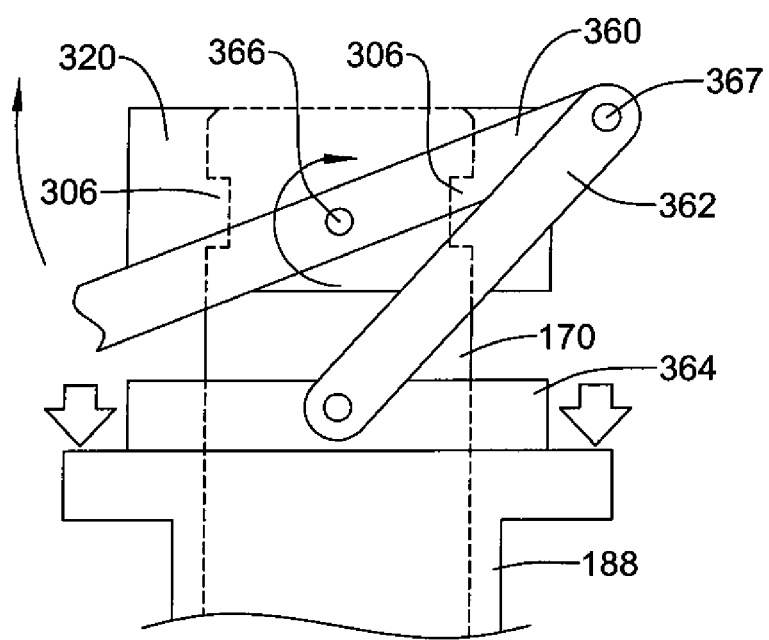

FIG. 10 depicts a cross-section of another reducer according to an exemplary embodiment of the invention, coupled to extender 170 and hollow shaft 188. The reducer includes a "z lever" configuration or assembly. Specifically, the reducer includes base 364 coupled to hollow shaft 188, and body 320 coupled to extender 170 (e.g., through locking members 306), lever bar 360, and truss 362.

Lever bar 360 couples at joint 367 to truss 362. Truss 362 couples to base 364 at joint. Lever bar 360 forms a lever, with a fulcrum at joint 366. The surgeon may lift lever bar 360, thus exerting downward force on truss 362 through joint 367. Truss 362 in turn exerts downward pressure on base 364 and hence on hollow tube 188. Lifting lever bar 360 also causes the lifting of body 320 and thus extender 170. Consequently, by lifting lever bar 362 by a desired amount, the surgeon can reduce the corresponding vertebral body.

Figure 11:
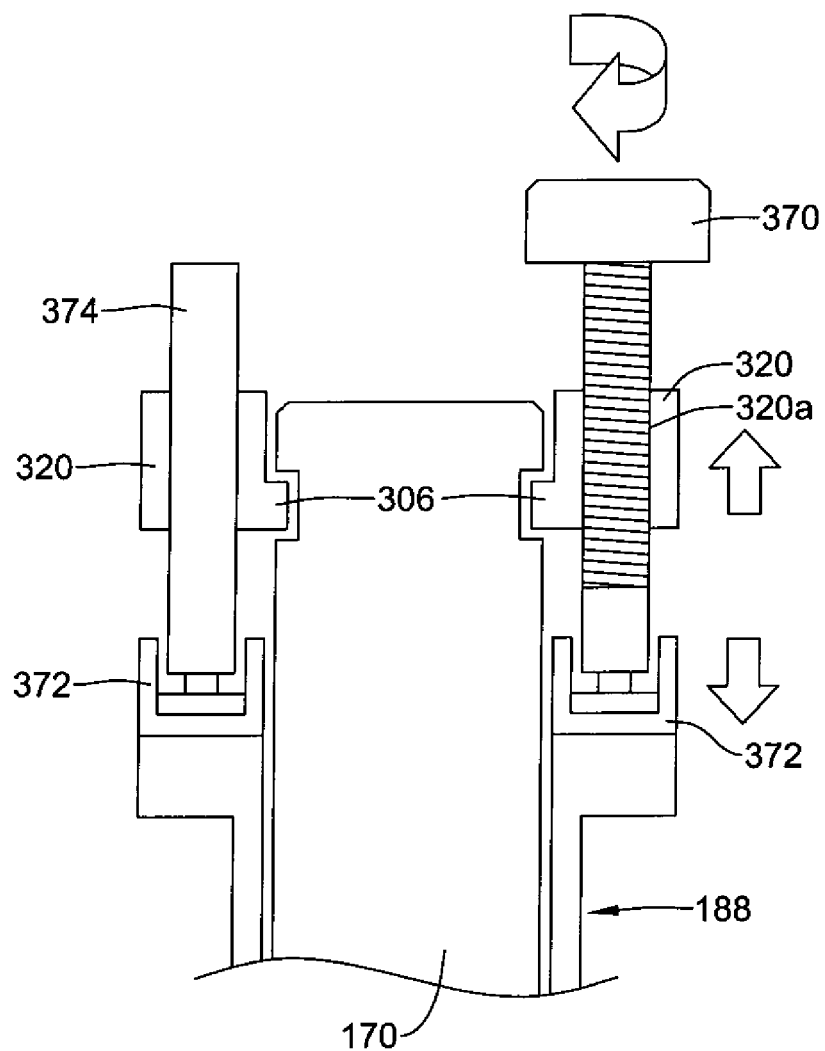

FIG. 11 shows a cross-section of another reducer according to an exemplary embodiment of the invention, coupled to extender 170 and hollow shaft 188. The reducer includes base 372 coupled to hollow tube 188, and body 320 coupled to extender 170.

The reducer further includes bolt or screw 370, whose threads engage with threaded portion 320A of body 320. An end of screw or bolt 370 couples to base 372. Slide pin 374 couples a portion of body 320 (opposite or distal end from screw or bolt 370 in the embodiment shown in FIG. 11) to base 372. Slide pin 374 provides stability to the mechanism and facilitates movement of body 320 with respect to base 372.

The surgeon may turn screw or bolt 370, which causes body 320 to move closer to (or farther from, depending on the type of threads of screw or bolt 370 and threaded portion 320A) base 372. Because extender 170 couples to body 320, movement of body 320 causes reduction of the corresponding vertebral body.

Figure 12:
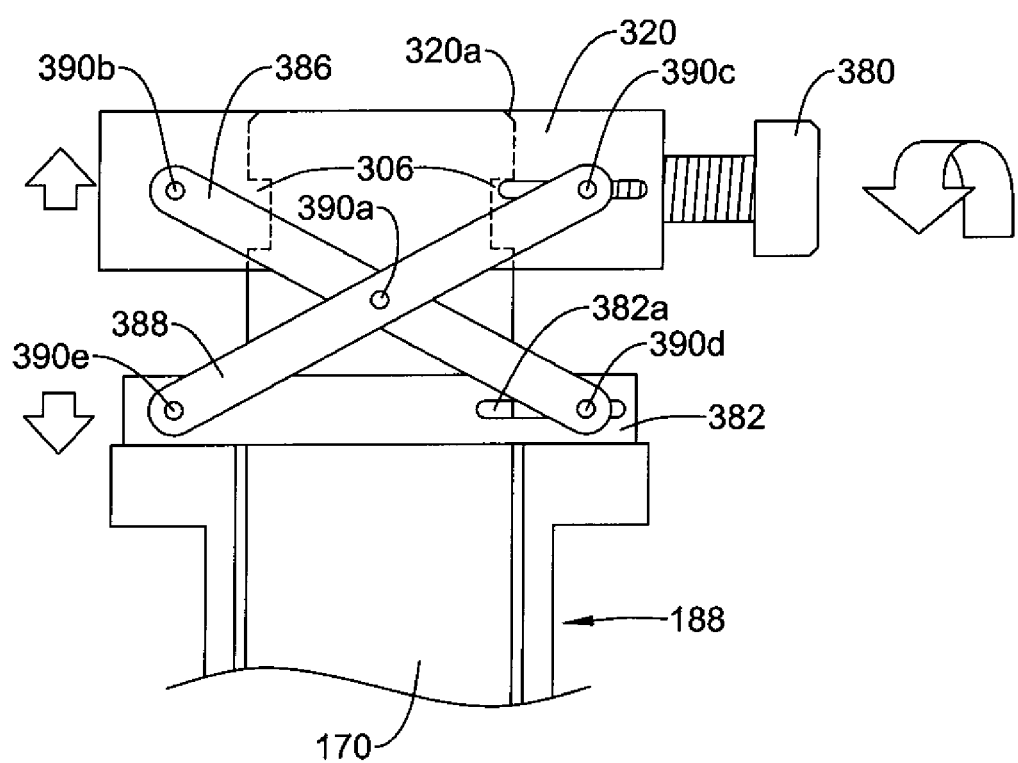

FIG. 12 illustrates a cross-section of another reducer according to an exemplary embodiment of the invention, coupled to extender 170 and hollow shaft 188. The reducer includes a "scissor jack" configuration or assembly. Specifically, the reducer includes base 382 coupled to hollow shaft 188, and body 320 coupled to extender 170 (e.g., through locking members 306), lever bar 386, screw or bolt 380, and lever bar 388.

Lever bar 386 and lever bar 388 couple to each other at joint 390A. Lever bar 386 couples to body 320 at joint 390B and to base 382 at joint 390D. Similarly, lever bar 388 couples to body 320 at joint 390C and to body 382 at joint 390E. By turning screw or bolt 380, the surgeon causes the location of joint 390C to move through slot 320A and the location of joint 390D to move through slot 382A, thus lifting body 320 with respect to base 380.

As noted, body 320 and base 380 couple, respectively, to extender 170 and to hollow shaft 188. Thus, the lifting of body 320 causes the lifting of extender 170 and therefore reduction of the corresponding vertebral body.

Figure 13:
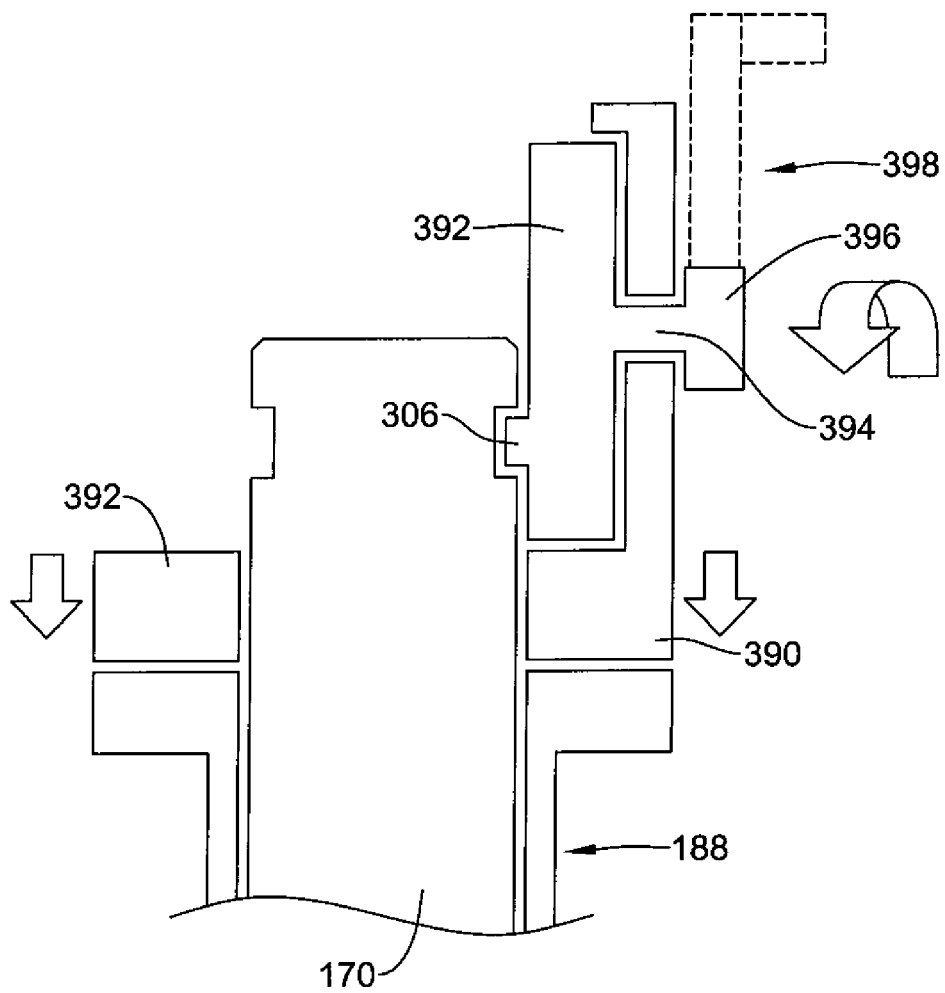

FIG. 13 shows a cross-section of another reducer according to an exemplary embodiment of the invention, coupled to extender 170 and hollow shaft 188. Generally speaking, the reducer includes an offset cam (locking member 306) assembly.

The reducer includes body 390 coupled to hollow shaft 188 and disk 392 coupled to extender 170. Disk 392 couples to one end of shaft 394, which passes through a bore or opening in body 390. Another end of shaft 394 couples to handle or member 396. Note that, rather than separate pieces (e.g., disk 392, shaft 394, and member 396), one may integrate or combine one or more of the components shown in FIG. 13. As merely one example, one may combine shaft 396 and disk 392 as one component.

Crank or handle 398 couples to member 396 and assists in turning shaft 394 and, hence, disk 392. Disk 392 couples to extender 170 via locking member 306 (e.g., a cam). Locking member 306 has an offset location with respect to shaft 394. Thus, turning shaft 394 causes the lifting of extender 170 and, hence, the reduction of the corresponding vertebral body.

Figure 14:
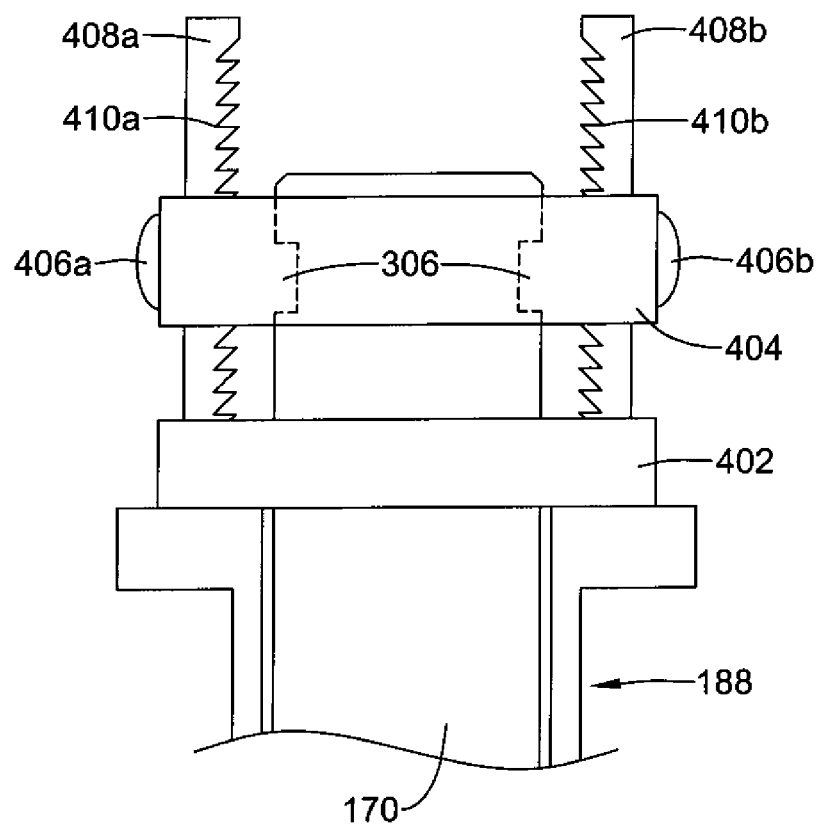
FIG. 14 shows a holding device according to one aspect of the inventive concepts for use with reducers according to the invention.

Another aspect of the invention relates to holding devices suitable for use with reducers according to various embodiments of the invention. FIG. 14 shows a cross section of an exemplary embodiment of a holding device. One may use the holder in conjunction or in combination with a reducer (e.g., the reducers in FIGS. 9, 10, and 13) in order to hold extender 170 in place (i.e., keep steady or hold constant the degree or amount of reduction).

The holder includes base 402 coupled to hollow shaft 188 and body 404 coupled to extender 170. Columns or bars 408A and 408B coupled body 404 to base 402. Body 404 may move along the length of columns 408A and 408B. Columns 408A and 408B have ratcheting teeth 410A and 410B, respectively. Ratcheting teeth 410A and 410B allow upward movement of body 404, but prevent its downward movement. Thus, the holder allows the surgeon to maintain a desired degree or amount of reduction once it is achieved.

The holder further includes release handles or members 406A and 406B. By activating or operating release handles 406A and 406B, the surgeon can cause the release of the ratcheting teeth 410A and 410B, respectively, thus allowing movement of body 404 with respect to base 402.

One may use a variety of mechanisms to couple the reducers according to the invention with extender 170, as persons of ordinary skill in the art who have the benefit of the description of the invention understand. As one specific case, one may couple the reducer to the extender in a releasable manner, such that the surgeon need not reverse some of the reduction procedure steps in order to decouple or release the reducer from the extender. The following description provides some examples of releasable coupling mechanisms that may be used with the reduction apparatus described above.

Figure 15:
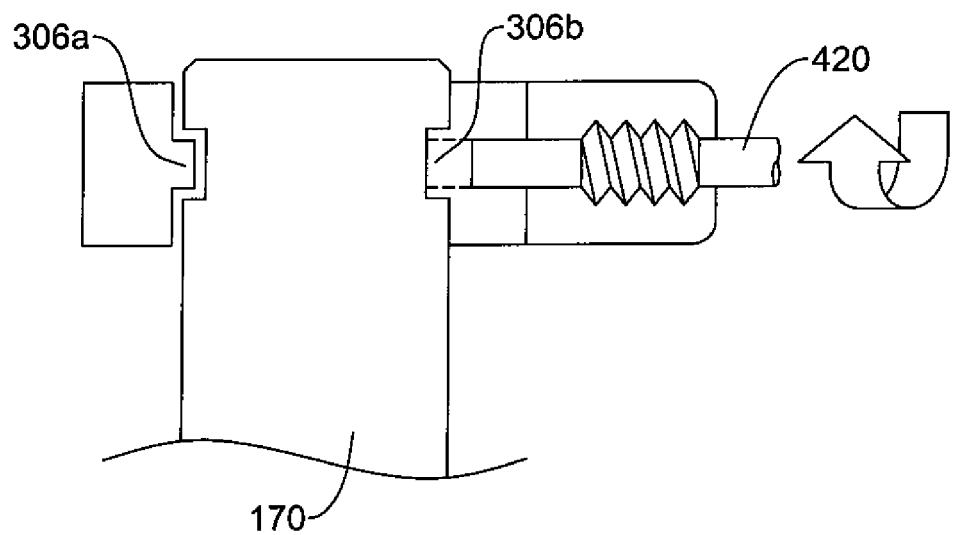
FIGS. 15-19 illustrate a plurality of attachment mechanisms according to exemplary embodiments of the invention.

FIG. 15 shows a cross-section of an attachment mechanism according to an exemplary embodiment of the invention. The attachment mechanism includes locking members 306A and 306B, and screw or bolt 420. Locking members 306A and 306B couple to extender 170, for example, through notches or other mechanisms in extender 170. Locking member 306A is stationary (e.g., part of the body of a reducer), but locking member 306B may move in response to force applied to it.

More specifically, by turning screw or bolt 420, one may cause it to contact and exert force against locking member 306B. Force applied against locking member 306B causes it to engage extender 170 and couple to it. Thus, by using the attachment mechanism, one may securely couple the reducer or other desired apparatus to extender 170 in order to perform the reduction procedure.

Figure 16:
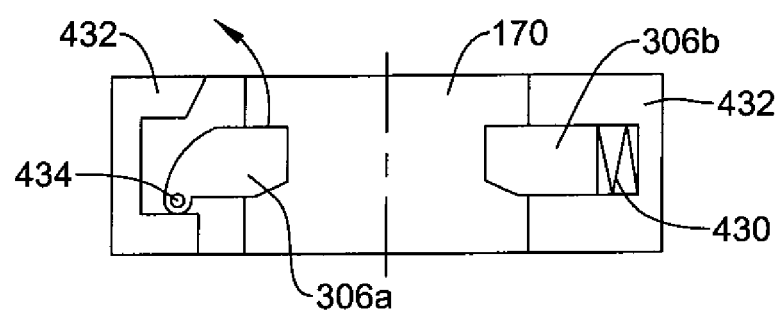

FIG. 16 shows a cross-section of other attachment mechanisms according to an exemplary embodiment of the invention. The apparatus shown in FIG. 16 illustrates two locking mechanisms. The locking mechanisms may be included within housing or member 432, for example, the body of a reducer.

One locking mechanism includes locking member 306A. Locking member 306A couples to housing 432 via a joint or hinge 434. Hinge 434 allows locking member 306A to swing or flip down. In this position, locking member 306A engages and couples to extender 170. Hinge 434 also allows locking member 306A to swing or flip up. In this position, locking member 306A disengages or uncouples from extender 170.

The second locking mechanism in FIG. 16 includes locking member 306B and biasing member or spring 430. Locking member 306B may slide within housing 432. When it slides towards extender 170, locking member 306B engages and couples to extender 170. Conversely, when it slides away from extender 170, locking member 306B disengages and uncouples from extender 170.

Spring 430 exerts some force against locking member 306B, which causes it to slide towards and couple to extender 170. When one desires to uncouple extender 170 from locking member 306B, one may slide away or push back locking member 306B from extender 170.

Figure 17:
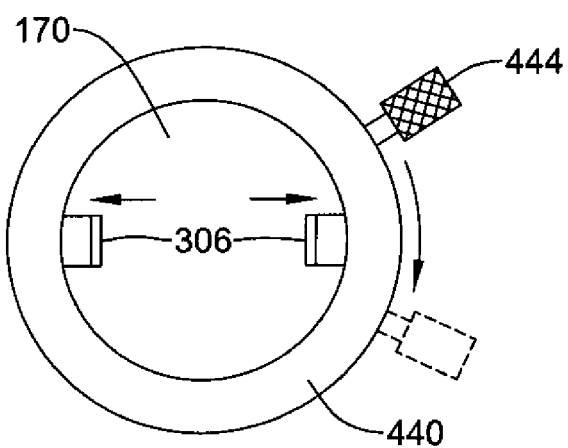

FIG. 17 depicts a cross-section of an attachment mechanism according to an exemplary embodiment of the invention. The attachment mechanism in FIG. 17 constitutes an "iris type" of mechanism, and includes locking members 306, ring 440, and handle or lever 444.

Turning handle 444 causes movement of locking members 306. More specifically, turning handle 444 in one direction (e.g., clockwise) causes locking members 306 to move towards each other, and thus engage and couple to extender 170. Turning handle 444 in the opposite direction (e.g., counterclockwise), however, causes locking members 306 to move away from each other, and thus disengage and uncouple from extender 170.

Figure 18:
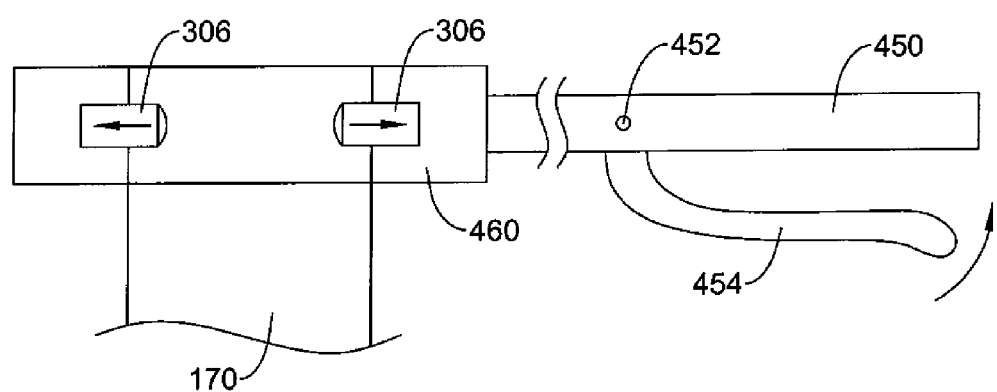

FIG. 18 depicts a cross-section of an attachment mechanism according to an exemplary embodiment of the invention. The attachment mechanism in FIG. 18 includes locking members 306, housing 460 (e.g., body or other part of a reducer), shaft 450, and handle 454.

Handle 454 couples to shaft 450 via hinge or joint 452. Engaging handle 454, e.g., by pulling it towards shaft 450, causes locking members 306 to move in one direction, for example, towards each other. As a result, locking members 306 engage with and couple to extender 170.

Disengaging handle 454, e.g., by pulling it away from shaft 450, causes locking members 306 to move in the opposite direction, for example, away each other. As a result, locking members 306 disengage and uncouple from extender 170.

Note that one may include in the apparatus shown in FIG. 18 mechanisms for holding handle 454 in a desired position, as desired, and as persons of ordinary skill in the art who have the benefit of the description of the invention understand. Examples of such mechanisms include ratchets, holding clamps, etc.

Figure 19:
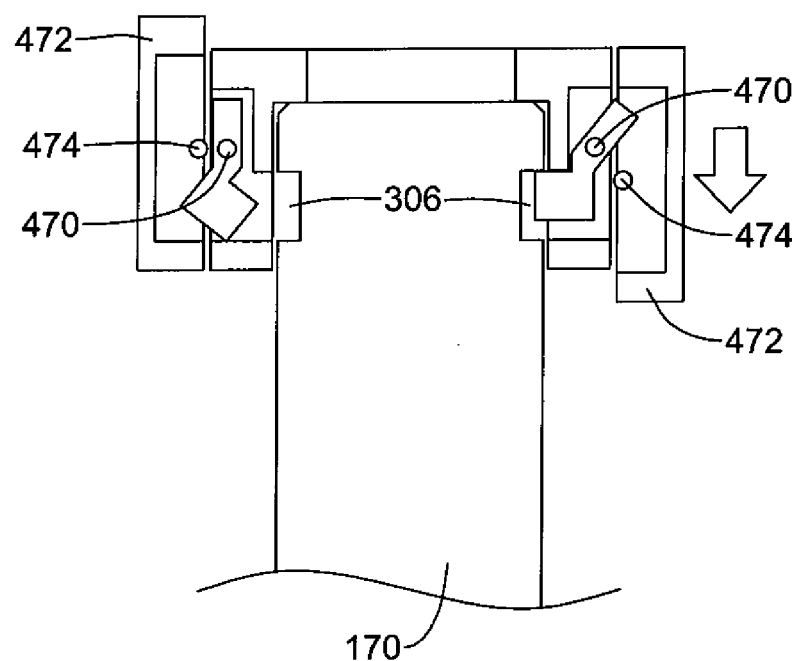

FIG. 19 depicts a cross-section of an attachment mechanism according to an exemplary embodiment of the invention. The attachment mechanism in FIG. 19 constitutes a "collet type includes locking members 306, sleeves 472, and engaging members 474. FIG. 19 shows one attachment mechanism in the locked position (the right side of FIG. 19), and another attachment mechanism in the unlocked position (left side of FIG. 19).

Each of locking members 306 may move around a respective joint or hinge 474. Generally, moving sleeves 472 causes engaging members 472 to contact locking members 306, form a collar or collet around them, and cause them to move. Movement of locking members 306 may cause them to engage and couple to extender 170, or to disengage and uncouple from extender 170. Note that the apparatus in FIG. 19 allows the surgeon to couple either side of the reducer to extender 170 independently of the other side.

As described, several embodiments of reducers according to the inventive concepts use threaded mechanisms or portions. By using a desired thread type and/or pitch, one may provide reducers with desired characteristics, as persons of ordinary skill in the art who have the benefit of the description of the invention understand.

For example, by using a relatively fine thread pitch, one may produce a reducer that causes a relatively small amount of reduction for a given amount of activation of the reducer (e.g., turning knob 302 in FIG. 3), and vice-versa. As noted, by using relatively fine thread pitches, one may allow the surgeon to fine-tune the reduction of the vertebral bodies with a relatively high degree of precision.

Furthermore, by varying the size or length of the threaded portion, one may produce reducers with desired characteristics. For example, a relatively long or large threaded portion would allow a relatively large reduction of the vertebral body, and vice-versa. This property allows reducers according to the inventive concepts to overcome the limited range of conventional reducers.

Various modifications and alternative embodiments of the invention in addition to those described here will be apparent to persons of ordinary skill in the art who have the benefit of the description of the invention. Accordingly, the manner of carrying out the invention as shown and described are to be construed as illustrative only.

Persons skilled in the art may make various changes in the shape, size, number, and/or arrangement of parts without departing from the scope of the invention described in this document. For example, persons skilled in the art may substitute equivalent elements for the elements illustrated and described here, or use certain features of the invention independently of the use of other features, without departing from the scope of the invention.

What is claimed is:

1. A rod reducing apparatus, comprising:
a screw assembly including a threaded shaft with a controlling member at a proximal end thereof and a rod contacting member at a distal end thereof; and
a grasping element including a distal end, a proximal end and a longitudinal axis extending therebetween, the distal end configured to grasp and detachably couple to a bone fastener and the proximal end connected to the screw assembly, wherein the rod contacting member defines an internal longitudinal passage configured to slidably receive the grasping element;
wherein rotation of the threaded shaft slides the rod contacting member along the longitudinal axis; and
wherein the controlling member is independently rotatable relative to the rod contacting member.

2. The apparatus of claim 1, wherein turning the controlling member causes the rod contacting member and the grasping element to move relative to each other in opposite directions.

3. The apparatus of claim 1, wherein the controlling member is a knob.

4. The apparatus of claim 3, wherein turning the knob in a first direction causes the rod contacting member to extend.

5. The apparatus of claim 1, wherein the rod contacting member has a substantially planar distal surface.

6. The apparatus of claim 1, further comprising at least a first locking member coupled to the screw assembly and configured to selectively engage the grasping element.

7. The apparatus of claim 1, further comprising a second locking member coupled to the screw assembly and configured to selectively engage the grasping element, wherein the first and second locking members are disposed on opposing sides of the screw assembly.

8. The apparatus of claim 1, wherein the screw assembly further includes a threaded body with threads complimentary to the threaded shaft.

9. A spinal reduction assembly comprising:
a bone fastener configured to be coupled to a vertebral body;
a collar configured to be coupled to the bone fastener, the collar including a slot for seating a rod;
a reducer configured to be coupled to the collar to seat the rod in the slot, the reducer comprising:
a screw assembly including a threaded shaft with a controlling member at a proximal end thereof and a rod contacting member at a distal end thereof; and
a grasping element including a distal end, a proximal end and a longitudinal axis extending therebetween, the distal end configured to grasp and detachably couple to the collar and the proximal end connected to the screw assembly, wherein the rod contacting member defines a first internal longitudinal passage configured to slidably receive the grasping element, wherein rotation of the threaded shaft slides the rod contacting member along the longitudinal axis.

10. The apparatus of claim 9, wherein turning the controlling member causes the rod contacting member and the grasping element to move relative to each other in opposite directions.

11. The apparatus of claim 9, wherein the controlling member is a knob.

12. The apparatus of claim 11, wherein turning the knob in a first direction causes the rod contacting member to extend.

13. The apparatus of claim 9, wherein the rod contacting member has a substantially planar distal surface.

14. The apparatus of claim 9, further comprising at least a first locking member coupled to the screw assembly and configured to selectively engage the grasping element.

15. The apparatus of claim 9, further comprising a second locking member coupled to the screw assembly and configured to selectively engage the grasping element, wherein the first and second locking members are disposed on opposing sides of the screw assembly.

16. The apparatus of claim 9, wherein the screw assembly further includes a threaded body with threads complimentary to the threaded shaft.

17. A method for reducing a rod into a rod receiving recess in a head of a bone fastener, the method comprising:
implanting at least one bone fastener into a bone of a patient and positioning a rod adjacent the bone fastener;
coupling a rod reducing apparatus to the bone fastener, over the rod, the rod reducing apparatus comprising:
a screw assembly including a threaded shaft with a controlling member at a proximal end thereof and a rod contacting member at a distal end thereof; and a grasping element including a distal end, a proximal end and a longitudinal axis extending therebetween, the distal end configured to grasp and detachably couple to the bone fastener and the proximal end connected to the screw assembly, wherein the rod contacting member defines an internal longitudinal passage configured to slidably receive the grasping element, wherein rotation of the threaded shaft slides the rod contacting member along the longitudinal axis; and rotating the threaded shaft to move the rod into a rod receiving recess in the bone fastener.

18. The apparatus of claim 6, wherein the rod contacting member and the grasping element are coupled via the first locking member to be rotationally stationary relative to each other.

19. The apparatus of claim 18, wherein the first locking member comprises at least one tab that extends into the grasping element.

20. The apparatus of claim 9, wherein the grasping element includes a second internal longitudinal passage concentric with the first internal longitudinal passage of the rod contacting member and the screw assembly includes an opening to permit access to the second internal longitudinal passage, whereby a shaft of a tool can be extended through the opening and into the first internal longitudinal passage and the second internal longitudinal passage to reach the collar.

* * * * *